US008327807B2

(12) United States Patent
Chiodo

(10) Patent No.: US 8,327,807 B2
(45) Date of Patent: Dec. 11, 2012

(54) CATHETER AND SEAL ASSEMBLY

(76) Inventor: Chris D. Chiodo, Warren, MI (US)

( * ) Notice: Subject to any disclaimer, the term of this patent is extended or adjusted under 35 U.S.C. 154(b) by 541 days.

(21) Appl. No.: 12/578,658

(22) Filed: Oct. 14, 2009

(65) Prior Publication Data

US 2010/0100072 A1 Apr. 22, 2010

Related U.S. Application Data

(60) Provisional application No. 61/196,371, filed on Oct. 17, 2008.

(51) Int. Cl.
*A01K 1/03* (2006.01)
(52) U.S. Cl. .................... 119/751; 119/417; 119/418
(58) Field of Classification Search .................. 119/751, 119/416, 417, 418, 420, 421, 752, 755, 756
See application file for complete search history.

(56) References Cited

U.S. PATENT DOCUMENTS

| 6,352,076 | B1 * | 3/2002 | French ................ 128/203.12 |
| 6,935,272 | B2 * | 8/2005 | Balto ................... 119/417 |
| 7,146,936 | B2 * | 12/2006 | Dazai et al. .......... 119/756 |
| 7,252,050 | B2 * | 8/2007 | Cole ................... 119/416 |
| 7,665,419 | B2 * | 2/2010 | Conger et al. ........ 119/419 |
| 7,703,414 | B2 * | 4/2010 | Kanno ................. 119/418 |
| 7,784,429 | B2 * | 8/2010 | Chiodo ................ 119/417 |
| 7,806,082 | B2 * | 10/2010 | Nelson ................ 119/420 |
| 2003/0229312 | A1 * | 12/2003 | Smith et al. ......... 604/152 |
| 2010/0101500 | A1 * | 4/2010 | Sannie et al. ........ 119/420 |

\* cited by examiner

*Primary Examiner* — Yvonne Abbott
(74) *Attorney, Agent, or Firm* — Lawrence J. Shurupoff

(57) ABSTRACT

A laboratory specimen sealed within a chamber on an animal holder may be injected or otherwise administered material such as drugs and radioactive imagining materials from the ambient, or outside the chamber, through a sealed catheter assembly. The animal holder can be mounted on imaging machines such as MRI, X-ray, PET, CT and like imaging machines. Biologically contaminated animals are isolated within the chamber from the ambient, yet may be injected from outside the chamber thereby protecting lab technicians from contamination and isolating the animal from additional contamination from an ambient environment, such as an imaging laboratory.

7 Claims, 3 Drawing Sheets

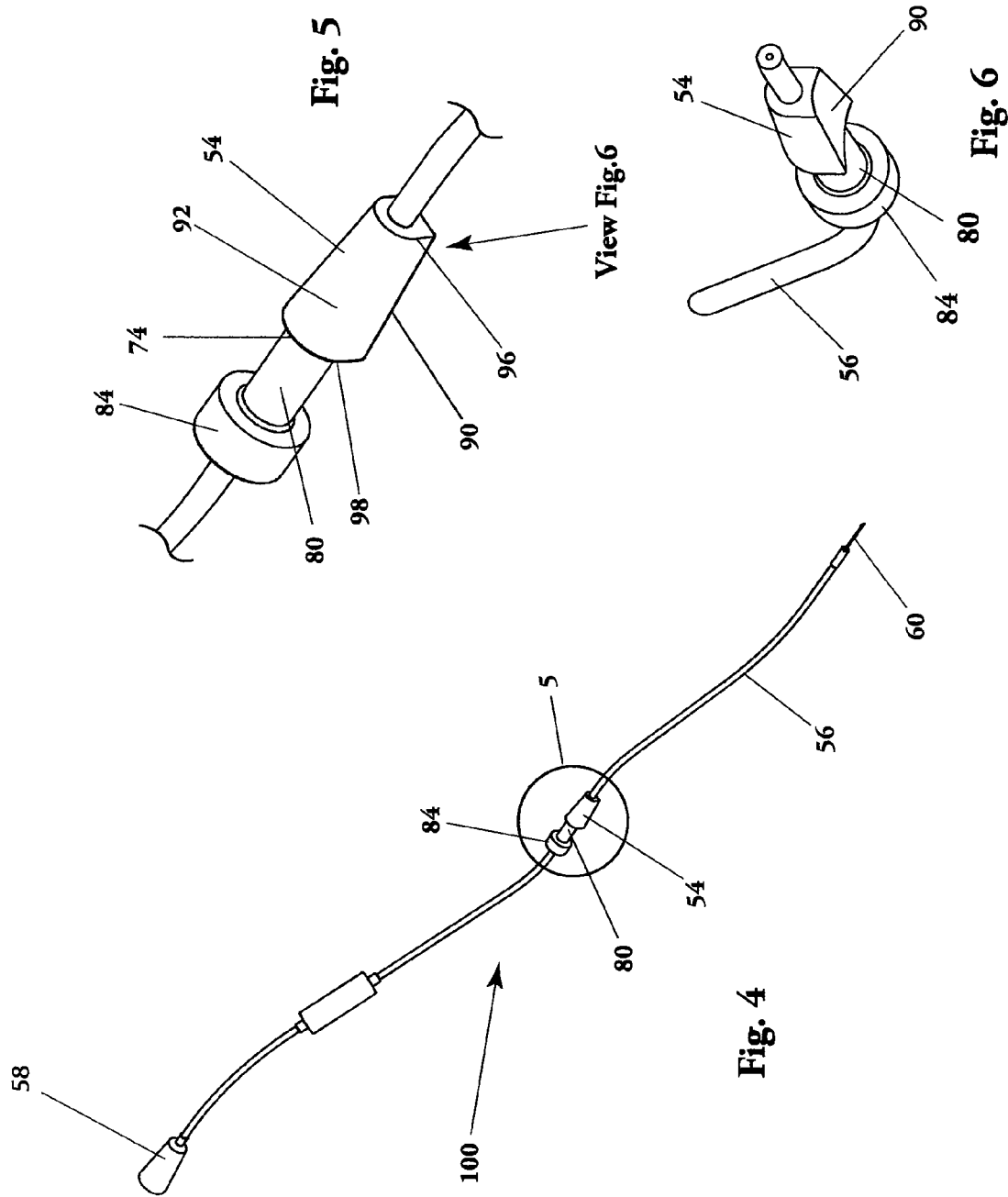

CATHETER AND SEAL ASSEMBLY

CROSS REFERENCE TO RELATED APPLICATIONS

This application claims the benefit and priority of provisional patent application No. 61/196,371 filed Oct. 17, 2008, and which is incorporated herein by reference in its entirety.

BACKGROUND

A need exists for a catheter which can be used to inject laboratory animals isolated within imaging chambers constructed for use in imaging machines such as MRI, X-ray, PET, CT and the like. In some studies, it is necessary to isolate a laboratory specimen, such as a mouse or rat, within a hermetically-sealed container during imaging procedures. Such test specimens may be biologically contaminated and should not be exposed to ambient.

During such studies, it is common to inject the specimen in its tail vein with various materials, including radioactive materials, which enhance the quality of images of the specimen produced by an imaging machine. After imaging is complete, it is generally desirable to discard the catheter as it may be contaminated with pathogens, injectates and the like.

BRIEF DESCRIPTION OF THE DRAWINGS

In the drawings:

FIG. 4 is a perspective view of a catheter and seal assembly such as shown in FIG. 1;

FIG. 5 is an enlarged view of region 5 of FIG. 4; and

FIG. 6 is a perspective end view of the seal of FIG. 5.

In the various view of the drawings like numerals designate like or similar parts.

DESCRIPTION OF A REPRESENTATIVE EMBODIMENT

Figure 1:
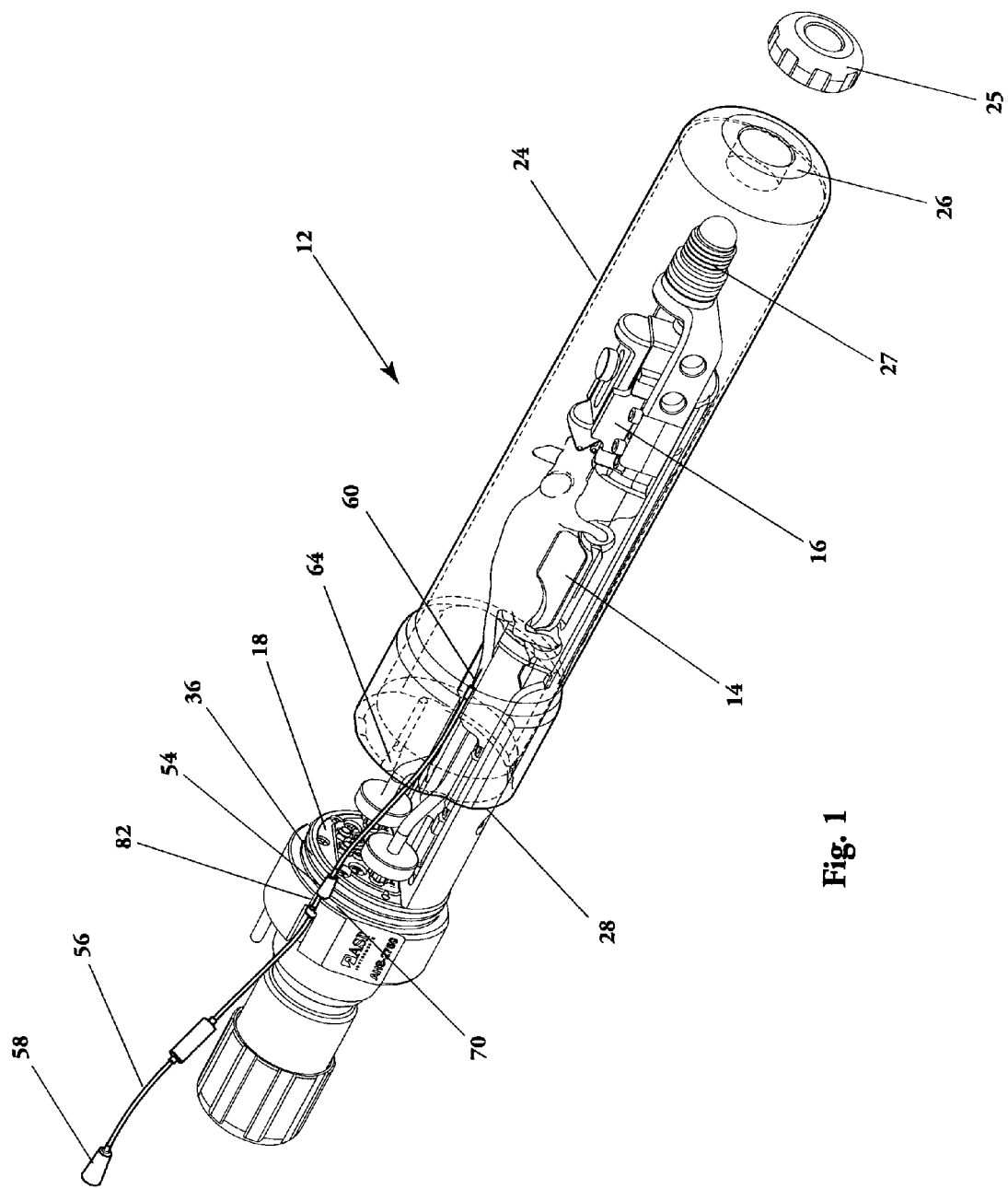
FIG. 1 is a perspective view of an animal holding system in a partially open position showing the location of a catheter and seal assembly thereon constructed in accordance with this disclosure.

As seen in FIG. 1, a modular specimen holder or animal holding system 12 is constructed to be removably and selectively mountable to a positioning receiver assembly which is adapted for mounting on or positioned within an imaging machine. The animal holding system 12 includes a specimen alignment bed 14 having a specimen retention assembly 16 for holding a specimen's head in place during imaging.

An interconnection panel 18 includes electrical and fluid ports and connectors for monitoring, treating and conditioning a specimen during imaging. Sensor leads, warming air and anesthesia gas can be channeled through the interconnection panel 18. A specimen, such as a mouse or rat, can be hermetically enclosed while on the alignment bed 14 with a cylindrical tube 24 which can form a hermetic seal around the specimen. Tube 24 is open at one end 26 adjacent the specimen's head to receive threaded shaft 27 and open at its opposite or rear end 28. Tube end 26 is hermetically sealed by O-rings on shaft 27 when threaded end cap or nut 25 is torqued down on shaft 27. The O-rings form a seal with an internal cylindrical collar extending inwardly from the end wall 26. The tube 24 can be formed of thin transparent plastic so as to be low cost and potentially disposable after one or more imaging procedures.

Figure 3:
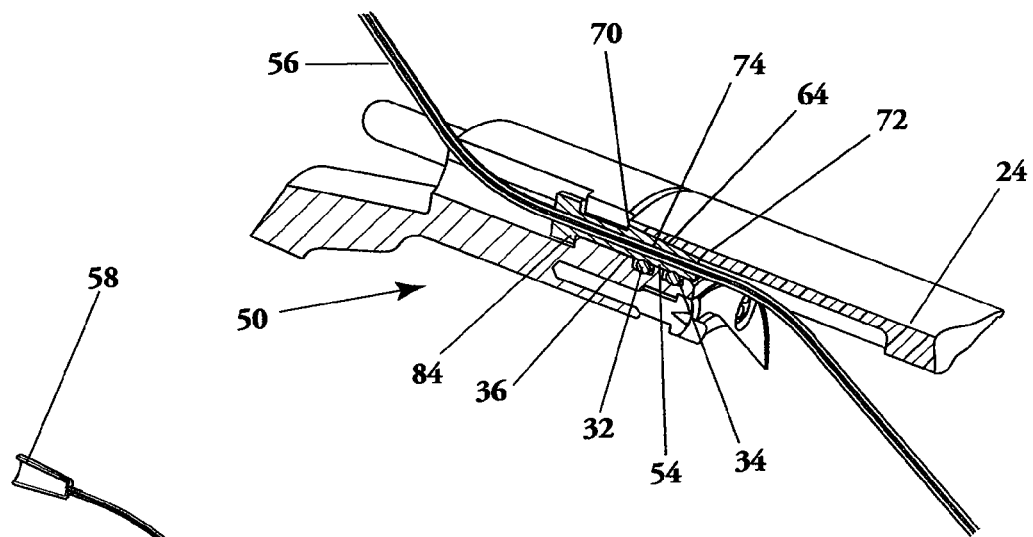
FIG. 3 is an enlarged view of region 3 of FIG. 2.
Figure 2:
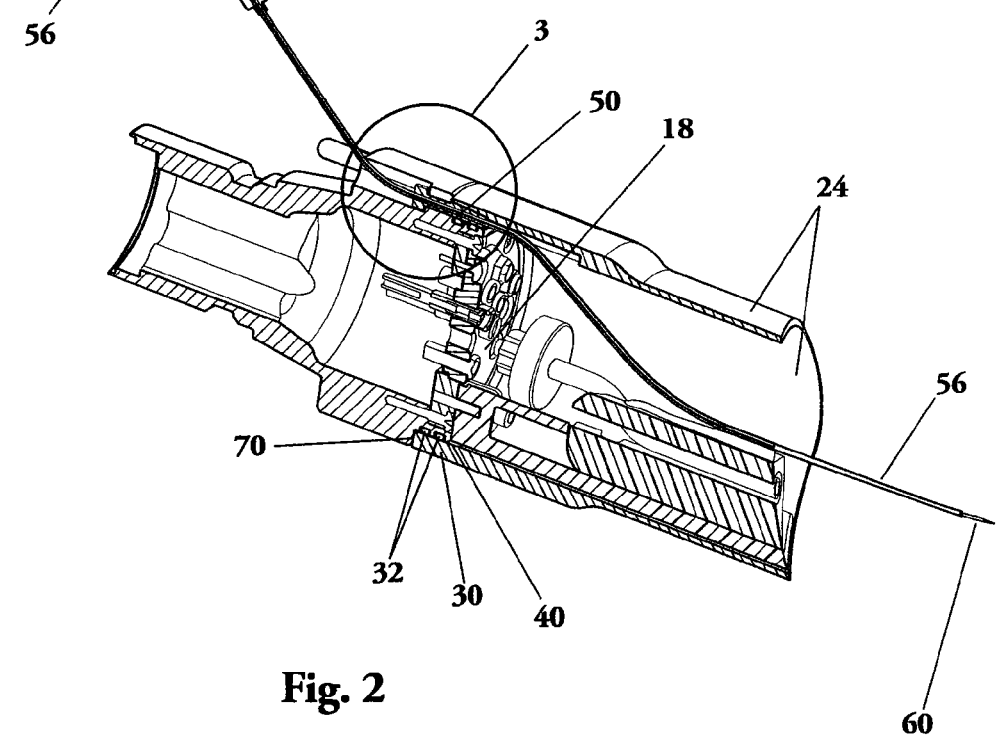
FIG. 2 is a partial view in axial section of the animal holding system of FIG. 1 in a hermetically closed position showing the arrangement of a catheter and seal assembly extending from the ambient surroundings into a hermitically sealed animal holding chamber.

As seen in FIG. 2, a first hermetic seal 30 is formed between the animal holding system 12 and tube 24. Seal 30 is formed by one or more o-rings 32 seated in annular circumferential grooves 34 (FIG. 3) provided in an annular wall 36 at a rear end portion of the animal holding system 12. In the example shown, wall 36 can be an outer portion of the interconnection panel 18. Hermetic seal 30 is formed by a simple axial sliding friction fit between the inner wall 40 (FIG. 2) of tube 24 and the o-rings 32, which are compressed within grooves 34 and against wall 40.

In order to accommodate a remote catheter which communicates with the interior of tube 24 and with the external ambient environment, a second hermetic seal assembly 50 (FIGS. 2 and 3) is provided along, over and between the first seal 30 and the tube 24. The second seal assembly 50 includes a soft, easily axially and radially resilient, compressible, elastomeric plug 54 provided on or over a catheter tube 56. The catheter tube 56 can include a needle 60 at one axial end portion for insertion into a specimen, such as within the tail vein of a laboratory mouse immobilized on the animal bed 14, as shown in FIG. 1. A hypodermic needle or drip tube can be used to introduce material into the other axial end of the tube 56 such as through a fluid fitting 58.

The second seal assembly 50 also includes a recess or pocket 64 (FIG. 1) provided on the rear end 28 of tube 24. Pocket 64 can be formed to compliment, match and compress the outer contours of the plug 54. That is, pocket 64 and plug 54 are dimensioned to form a compressive interference fit that forces the plug 54 radially inwardly against the o-rings 32 and against wall 36 to form the second hermetic seal assembly 50. At the same time, the plug 54 is compressed against the inner walls of pocket 64 to complete the seal assembly 50 as tube 24 is axially moved over wall 36 and radially compresses the O-rings 32.

The axial length of pocket 64 is less than the axial length of the plug 54 so that when the tube 24 is fully axially seated against the radial wall 70, the axially-tapered inner wall 72 of pocket 64 axially pushes the outer tapered wall 74 of plug 54 toward radial wall 70 to form a sealing interface between the rear wall 98 (FIG. 5) of plug 54 and the radial wall 70.

As seen in FIGS. 4, 5 and 6, plug 54 can be overmolded or assembled on an outer wall of the catheter tube 56. A locating sleeve 80 can be integrally formed with the plug 54 to fit within a positioning slot 82 (FIG. 1) on the rear end of the animal alignment system 12, such as within a slot in the radial wall 70 and in wall 36. A radically enlarged annular flange 84 is located at one end of a radially reduced or radially necked-down sleeve 80 and a radially enlarged portion of plug 54 is located at the other end of sleeve 80. The axial length of sleeve 80 is about the same as the axial length of the positioning slot 82. This dimensioning axially and circumferentially positions the plug 54 on the walls 36 and 70.

In the example shown in the drawings, the plug 54 has a contoured or concave radially inner bottom wall 90 (FIG. 6) which matches or compliments the cylindrical surface of the radial wall 36 against which it forms a seal, and an arched radially outer upper portion 92 bounded by a planar radial front wall 96 and a planar radial rear wall 98. Due to the axial taper of plug 54, the front wall 96 is smaller than the rear wall 98.

The upper portion 92 and bottom or radially inner wall 90 taper outwardly (circumferentially) from the smaller front wall 96 to the larger rear wall 98.

With the seal 50 as described above, a simple, inexpensive and disposable catheter and seal assembly 100 (FIG. 4) is provided for simple and effective treatment of laboratory animals held within an animal holding system 12.

What is claimed is:

1. An animal holding system, comprising:
   an animal holder comprising a bed for supporting an animal,
   a chamber surrounding said bed and carried by said animal holder;
   a first seal provided between said animal holder and said chamber;
   a catheter extending from outside said chamber to inside said chamber;
   a second seal provided on said catheter; and
   said first and second seals hermetically sealing said animal bed within said chamber.

2. The system of claim 1, wherein said chamber comprises a tube surrounding said animal holder.

3. The system of claim 1, wherein said first seal comprises an O-ring seal.

4. The system of claim 1, wherein said second seal comprises a resilient plug axially and radially compressed between said animal holder and said chamber.

5. The system of claim 4, further comprising a pocket formed between said animal holder and said chamber, and wherein said second seal is compressed within said pocket.

6. The system of claim 5, wherein said second seal engages and overlies said first seal.

7. The system of claim 1, further comprising a positioning slot formed in said animal holder and receiving a portion of said second seal.

* * * * *